United States Patent [19]

Falkow et al.

[11] Patent Number: 5,663,317

[45] Date of Patent: Sep. 2, 1997

[54] MICROORGANISM HAVING ATTENUATED INVASIVENESS

[75] Inventors: Stanley Falkow, Portola Valley, Calif.; Catherine A. Lee, Newton, Mass.

[73] Assignee: The Board of Trustees of the Leland Stanford Jr. Univ.

[21] Appl. No.: 295,760

[22] PCT Filed: Mar. 1, 1993

[86] PCT No.: PCT/US93/02265

§ 371 Date: Sep. 1, 1994

§ 102(e) Date: Sep. 1, 1994

[87] PCT Pub. No.: WO93/18165

PCT Pub. Date: Sep. 16, 1993

Related U.S. Application Data

[63] Continuation-in-part of Ser. No. 844,470, Mar. 2, 1992, abandoned.

[51] Int. Cl.$^6$ ..................................................... C12N 15/31
[52] U.S. Cl. ........................... 536/23.7; 935/9; 935/11
[58] Field of Search ..................... 536/23.7; 435/252.3, 435/252.8, 172.3, 320.1; 935/9, 11, 65

[56] References Cited

FOREIGN PATENT DOCUMENTS

| 0184086 | 11/1986 | European Pat. Off. | C12N 15/00 |
| WO9012867 | 11/1990 | WIPO | C12N 1/21 |
| A91/15572 | 10/1991 | WIPO | C12N 1/20 |

OTHER PUBLICATIONS

Groisman, E.A., et al., "Cognate Gene Clusters Govern Invasion of Host Epithelial Cells by *Salmonella typhimurium* and *Shigella flexneri*", *The EMBO Journal*, 12(10):3779–3787 (1993).

Stone, B.J., et al., "Identification of Novel Loci Affecting Entry of *Salmonella enteritidis* into Eukaryotic Cells", *Journal of Bacteriology*, 174(12):3945–3952 (1992).

Altmeyer, R.M., et al., "Cloning and Molecular Characterization of a Gene Involved in *Salmonella* Adherence and Invasion of Cultured Epithelial Cells", *Molecular Microbiology*, 7(1):89–98 (1993).

Betts, J., et al., "Identification of *Salmonella typhimurium* Invasiveness Loci", *Biotechnology Laboratory of the Department of Biochemistry and Microbiology*, University of British Columbia, (1992).

Neidhardt, F.C., et al., "*Escherichia coli* and *Salmonella typhimurium*, Cellular and Molecular Biology", 1:732–759. (1987) American Society for Microbiology, Washington DC.

Wilson, D.R., "Alternative Methods of Attenuating *Salmonella* Species for Potential Vaccine Use", *Res. Microbiol.* 141:827–830 (1990).

(List continued on next page.)

*Primary Examiner*—Mary E. Mosher
*Attorney, Agent, or Firm*—Flehr, Hohbach, Test, Albritton & Herbert; Richard F. Trecartin; Robin M. Silva

[57] ABSTRACT

The invention provides nucleic acids encoding one or more hyper-invasive genes within the hil locus (hyper-invasion locus) or fragments thereof, methods for making attenuated microorganisms and identifying such hyper-invasive nucleic acids as well as mutant microorganisms wherein one or more hyper-invasive genes within the hil locus are modified to attenuate the invasive phenotype of the microorganism. The methods of the invention utilize conditions which repress invasiveness in an otherwise invasive microorganism. The method comprises mutating an invasive microorganism to form a plurality of mutant microorganisms. The thus formed mutants are exposed to conditions which repress invasiveness of the parental invasive microorganism. At least one mutant microorganism is then detected which exhibits an increase in invasiveness as compared to the parental invasive microorganism. The site of mutation in the genome of the mutant microorganism is then determined to localize and identify one or more hyper-invasive genes within the hil locus of the invasive microorganism.

4 Claims, 1 Drawing Sheet

OTHER PUBLICATIONS

Elsinghorst, E.A., et al., "Penetration of Human Intestinal Epithelial Cells By *Salmonella:* Molecular Cloning and Expression of *Salmonella typhi* Invasion Determinants In *Escherichia coli*", *Proc. Natl. Acad. Sci. USA,* 86:5173–5177 (1989).

Hormaeche, C.E., et al., "Live Attenuated Salmonella Vaccines and Their Potential As Oral Combined Vaccines Carrying Heterologous Antigens", *Journal of Immunological Methods,* 142:113–120 (1991).

Miller, I., et al., "Isolation of Orally Attenuated *Salmonella typhimurium* Following *TnphoA* Mutagennesis", *Infection and Immunity,* 57(9):2758–2763 (1989).

Galan, J.E., et al., "Distribution of the *invA, –B, –C,* and *–D* Genes of *Salmonella typhimurium* among other *Salmonella* Serovars: invA Mutants of *Salmonella typhi* are Deficient for Entry into Mammalian Cells", *Infection and Immunity,* 59(9):2901–2908 (1991).

Galan, J.E., et al., "Cloning and Molecular Characterization of Genes Whose Products Allow *Salmonella typhimurium* to Penetrate Tissue Culture Cells", *Proc. Natl. Acad. Sci. USA,* 86:6383–6387 (1989).

Lee, C.A., et al., "Identification of a *Salmonella typhimurium* Invasion Locus by Selection for Hyperinvasive Mutants", *Proc. Natl. Acad. Sci. USA,* 89:1847–1851 (1992).

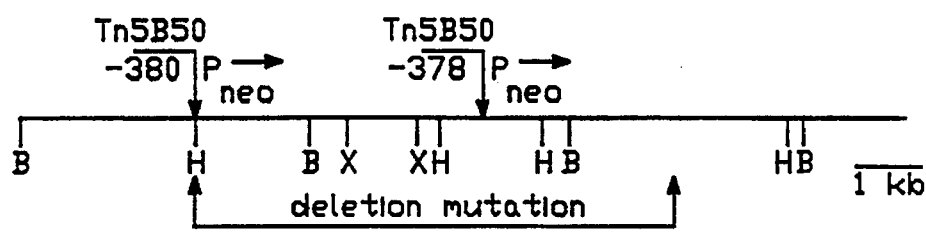
FIG.—1A
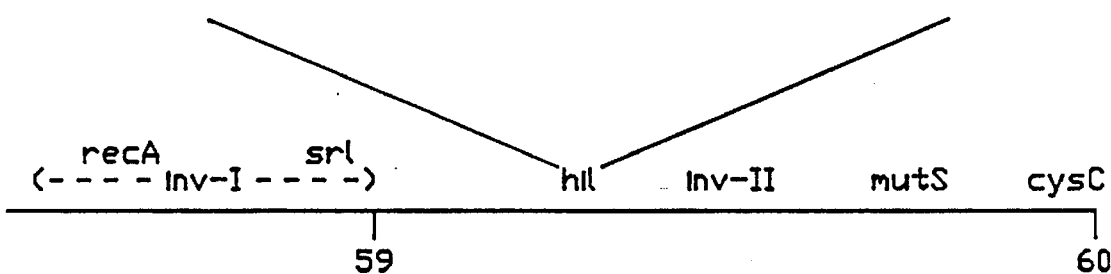
FIG.—1B

MICROORGANISM HAVING ATTENUATED INVASIVENESS

This application is a U.S. National Stage application under 35 U.S.C 371 of PCT/US93/02265, filed Mar. 1, 1993, which is a continuation-in-part of U.S. application Ser. No. 07/844,470, filed Mar. 2, 1992, now abandoned.

TECHNICAL FIELD

The invention relates to microorganisms having attenuated invasiveness.

BACKGROUND

For many species of microorganisms, invasion and survival within mammalian cells is central to establishing a successful host-parasite relationship. The invasive character of pathogens, while deleterious to the health and viability of host cells, does provide a mechanism for transfer of molecules and aggregates across an intact cellular membrane. Thus, microorganisms having an attenuated invasive phenotype which minimizes the deleterious effect of infection through invasion are useful as a vaccine for the pathogen itself or as a vehicle for transporting molecules of interest into a host organism or its cells.

For example, a microorganism having attenuated invasiveness can provide for the transfer of genetic material into a mammalian host or its cells. In this manner, novel genetic capabilities can be imparted to the host. One capability of interest is the synthesis of surface membrane proteins or envelope proteins of pathogens. These proteins can then serve as antigens to provide a strong immune response, without the host having to suffer the effects of infection by the pathogen.

A number of microorganisms are known to invade mammalian cells including Yersinia, Shigella and Salmonella. The invasion of epithelial cells by *Yersinia pseudotuberculosis* is reported by Bovallius and Nilson, (1975) *Can. J. Microbiol.* 21:1997–2007 and Bolin et al., (1982) *Infect. Immun.* 37:506–512. Isberg and Falkow, (1985) *Nature* 317:262–264 and Isberg et al., (1987) *Cell* 50:769–778 describe the invasion locus of *Yersinia pseudotuberculosis*. Falkow et al., Reviews of Infectious Diseases, 9 Supp. 5 S450–S455 (1987) describes the Yersinia gene inv. Miller and Falkow, (1988) *Inf. and Imm.* 56:1242–1248 describe a second invasion gene named ail (for attachment invasion locus). Miller et al., (1989) *Science* 243:916–922 describe factors involved with virulence of bacterial pathogens. The nucleotide sequence of the *Y. enterocolitica* ail gene is described in Miller et al., (1990) *Bacteriology* 172:1062–1069. See also Miller et al., (1989) *Infect. and Immun.* 57:121–131.

The factors associated with Shigellae invasiveness are described by Hale et al., (1983) *Infect. Immun.* 40:340–350. Sansonetti et al., (1983) ibid 39:1392–1402 and Maurelli et al., (1985) ibid 49:164–171 describe the manipulation of the plasmid in Shigellae encoding functions essential for invasiveness.

Salmonella penetrate the intestinal epithelial barrier during infection. Takeuchi, A. (1967) *M. J. Pathol.* 50:109–136; Worton, K. J., et al. (1989) *J. Med. Microbiol.* 29:283–294. The interactions between Salmonella and the non-phagocytic cells lining the mucosal surface of the bowel, however, can be studied experimentally since Salmonella enter cultured epithelial cells in vitro. Finlay, et al. (1988) *J. Cell Biol.* 107:221–230; Finlay, et al. (1988) *J. Infect. Dis.* 162:1096–1106. In one laboratory strain of Salmonella *typhimurium*, which had undergone many genetic manipulations and was found to be non-invasive, complimentation of the defect by genes from a virulent strain led to the identification of a locust comprising of seven genes that is required for bacterial invasion and virulence. Galan, J. et al. (1989) *Proc. Natl. Acad. Sci USA* 86:6383–6387. Finlay et al., *Science* 243:940–943 describe an invasion gene of Salmonella.

Many attempts have been made to clone Salmonella genes into *E. coli* and to confer the ability to enter. epithelial cells. Such an approach was successful in identifying invasion factors in Yersinia species. Isberg and Falkow (1985), ibid. and Miller and Falkow (1988), ibid. Thus far, only one locus, from *Salmonella typhi*, has been identified by this approach. Elsinghorst, E. A., et al. (1989) *Proc. Natl. Acad. Sci. USA* 86:5173–5177. In addition to the aforementioned genetic factors, it has been determined that Salmonella invasiveness is regulated by oxygen such that bacteria grown aerobically are less invasive than bacteria grown under oxygen-limiting conditions. Lee and Falkow (1990) *Proc. Natl. Acad. Sci. USA* 87:4304–4308; Ernst et al. (1990) *Infect. Immun.* 58:2014–2016; and Schiemann, D. A. et al. (1991) *Infect. Immun.* 59:437–440.

In addition, St. Geme, J. W. et al. (1990) *Infect. and Immun.* 58, 4036–4044 describe the adherence and invasion of *Haemophlilus influenzae* into human epithelial cells. For a review of bacterial invasive strategies, see Finlay and Falkow (1989) *Microbiological Reviews* 53:210–230.

SUMMARY OF THE INVENTION

The invention provides nucleic acids encoding one or more hyper-invasive genes within the hil locus (hyper-invasion locus) or fragments thereof, methods for making attenuated microorganisms and identifying such hyper-invasive nucleic acids as well as mutant microorganisms wherein one or more hyper-invasive genes within the hil locus are modified to attenuate the invasive phenotype of the microorganism.

The methods of the invention utilize conditions which repress invasiveness in an otherwise invasive microorganism. The method comprises mutating invasive microorganism to form a plurality of mutant microorganisms. The thus formed mutants are exposed to conditions which repress invasiveness of the parental invasive microorganism. At least one mutant microorganism is then detected which exhibits an increase in invasiveness as compared to the parental invasive microorganism. The site of mutation in the genome of the mutant microorganism is then determined to localize and identify one or more hyper-invasive genes within the hil locus of the invasive microorganism.

The foregoing method has been used to identify the hil locus in Salmonella. When this locus is expressed by a constitutive promoter, the mutant Salmonella exhibits an increased invasiveness phenotype in vitro under conditions which otherwise suppress invasiveness in the wild-type organism. When the hil locus is mutated, e.g., by way of deletion of one or more nucleotides, the resultant microorganism has a phenotype wherein the mutant has decreased invasiveness, as compared to the comparably grown parental strain, even under low oxygen conditions which are known to enhance invasiveness.

BRIEF DESCRIPTION OF THE DRAWINGS

FIG. 1A depicts the restriction map of 20 kb of *S. typhimurium* chromosomal DNA encompassing the hil locus. B, BamH1; H, HindIII; X, XhoI. The position and orientation of Tn5B50 insertions are shown above the chromosomal map. The limits of deletion mutation are shown below the chromosomal map. Presumably, placement of Tn5-428 between the rightmost BamHI sites occurred prior to deletion between 1550 elements of Tn5B50-380 and the Tn5.

FIG. 1B depicts the genetic map of genes in the 59–60 minute region of the *S. typhimurinm* chromosome. The inv-1 locus consists of four genes interspersed with recA and srl. The orientation of the hil restriction map with respect of the other genes is not known.

DESCRIPTION OF THE SPECIFIC EMBODIMENTS

In one aspect, the invention provides methods for making microorganisms having attenuated invasiveness and methods for identifying nucleic acids encoding one or more hyper-invasive genes within a hyper-invasion locus (hil). As used herein, a "hyper-invasion locus" refers to a region within the genome of an invasive microorganism which is identified according to the methods described herein. The hyper-invasion locus contains one or more hyper-invasive genes (also referred to as hil genes) which have not previously been identified as being responsible for the invasive phenotype. Thus, hil genes exclude other invasive genes such as inv and ail from Yersinia. A characteristic of a hyper-invasive gene is its ability to enhance the invasive phenotype when expressed under conditions which otherwise repress the invasive phenotype. Invasiveness is believed to be due to the expression of genes which encode surface proteins which mediate attachment and invasion. Such invasive genes are also believed to be regulated, in some instances, by activator genes which are responsive to environmental factors. A hyper-invasive gene therefore can encode either an invasive hil gene (encoding an invasive membrane protein which is sufficient to confer the invasive phenotype) or an activator hil gene which regulates one or more invasive genes required for invasion.

The source of hil genes can be from any invasive microorganisms. Such organisms include Yersinia, Chlamydia, *Legionella pneumophila, Listeria monocytogenes, Mycobacterium tuberculosis, Haemophilus influenzae, Mycobacterium leprae, Salmonella typhosa, Salmonella typhimurium,* enteropathogenic *E. coli* (EPEC strains), *Brucella abortus, Cryptococcus neoformans, Histoplasma capsulation, Candida albicans, Tripanosoma cruze, Toxaplasma gondi, Leishmania donovani,* etc. Thus, the source organisms for hii genes may be bacterial, fungal or protozoan.

The methods of the invention can be employed with any invasive microorganism whose invasiveness can be reduced or repressed by exposing the microorganism to specific environmental conditions. For example, it is known that Salmonella invasiveness is regulated by oxygen such that bacteria grown aerobically are less invasive than bacterial grown under oxygen-limiting conditions, e.g. less than about 1% oxygen. Similarly, Shigella invasiveness is known to be down regulated by decreasing temperature. Yersinia invasiveness is also modulated by temperature but in a somewhat more complex manner. While an increase in temperature decreases invasiveness of Yersinia as mediated by the inv gene, invasiveness mediated by the ail locus is increased. However, one skilled in the art can readily adjust the temperature of Yersinia cultures to decrease the overall invasiveness of the microorganism in a selected invasive assay system. Other potential invasive microorganisms which can be utilized in the methods of the invention include enteropathogenic *E. coli* (EPEC) which are closely related to Shigella.

In the methods of the invention, a selected invasive microorganism is first mutated to produce a plurality of mutant microorganisms. A particularly preferred mutation comprises introduction of a transposon which contains a constitutive or inducible promoter at or near one end of the transposon. In addition, the transposon generally contains a selection marker which permits selection of those invasive microorganisms successfully transformed with the transposon. When a transposon containing a constitutive promoter is integrated into the genome of the microorganism, the promoter is capable of causing expression of genomic sequences situated downstream from the promoter sequence. The plurality of mutated microorganism, accordingly, contains a sub-population of individual microorganisms wherein one or more genomic sequences are constitutively activated. The promoter from the neomycin resistance gene is an example of a constitutive promoter. However, other promoters, including inducible promoters such as the promoter from the lac Z gene can be used. When an inducible promoter is used, conditions to induce the promoter should be imposed upon the mutant microorganisms prior to and/or during the following step.

After forming the plurality of mutant microorganisms, the mutants are exposed to conditions which repress invasiveness in the parental invasive microorganism. In the case of Salmonella, such conditions include exposing the culture to aerobic conditions. In the case of Shigella and Yersinia, changes in culture temperature can also be used to down regulate invasiveness.

The mutant microorganisms are then assayed to determine the invasiveness of the mutant microorganisms as compared to the parental invasive microorganism. Any invasive assay system can be used but preferably will comprise an in vitro assay which is capable of detecting a change in invasiveness of the mutant microorganisms for cultured mammalian cells as compared to the parent organism. For Salmonella, numerous in vitro assays have been developed for quantifying the ability of Salmonella to adhere to and enter cultured mammalian cells. See Lee and Falkow (1990) *Proc. Natl. Acad. Sci. USA* 87:4304–4308 and references cited therein. A preferred cell line for testing invasiveness is HEp-2 cells (ATCC CCL23), a cell line established from human epidermoid carcinoma. Host cells which can be used to measure invasiveness of Yersinia include the cell lines disclosed by Isberg, et al. (1987) *Cell* 50:769–778. Cell lines appropriate for assaying invasiveness of Shigella include those disclosed in Finlay and Falkow (1989) *Microbiological Reviews* 53:210–230.

In general, the parental strain from which the mutant microorganisms are derived is subjected to the same experimental conditions in parallel with those of the mutant microorganism. Invasiveness can be measured by directly determining the number of intracellular microorganisms. More conveniently, a selection procedure is used to indirectly determine invasiveness. The selection procedure is based upon protection of intracellular bacteria from exposure to an antibiotic which is incapable of traversing the cellular membrane of the cultured mammalian cell. In general, the methods provides for contacting the parent microorganism or mutant microorganism with a layer of appropriate cells under conditions which repress invasiveness of the parental organism but which allow for invasion of the host cells by mutant microorganisms if a hyper-invasive phenotype is produced by the mutation. Thereafter, the cell culture is contacted with an antibiotic such as gentamicin for a period of time which is sufficient to kill extracellular bacteria. Any intracellular bacteria are thereafter released by treatment with a mild detergent, e.g., a nonionic detergent generally at a concentration in the range of about 0.1 to 2%, more conveniently in the range of about 0.5 to 1.5%, in an aqueous medium. Viable bacteria are then quantitated by plating for CFU on an appropriate agar medium. An increase in invasiveness comprises any statistically significant increase in the invasive capability of a mutant microorganism as compared to the parent strain. However, based upon the results observed with Salmonella, an increase in invasiveness will generally result in at least a 10-fold increase in invasiveness relative to the parental strain and may be as high as 50-fold or greater.

The mutant microorganisms so obtained have attenuated invasiveness which is greater than that of the parental organism. Such microorganisms are useful as vaccines or to deliver molecules of interest to an organism or its cells. However, to the extent that the increased invasiveness of such microorganisms is deleterious to the host organism, it is preferred that other mutations be included within the genotype to attenuate the survival of such organisms in a mammalian host. Such further mutations include one or more non-reverting mutations in a biosynthetic pathway which produces a metabolite not otherwise found in sufficient quantity in a mammalian host to permit survival of the microorganism. Examples include inversions and or deletions in one or more genes in the pathway for the synthesis of aromatic amino acids alone or in combination with a similar mutation in a pur gene. Protocols for generating microorganisms having such attenuated survival are described in U.S. Pat. Nos. 4,550,081, 4,735,801, 4,837,151 and 5,077,044.

Such hyper-invasive mutant microorganisms, however, can also be used to determine the nucleic acid sequence of one or more hyper-invasive genes responsible for the observed phenotype. Thus, in one aspect of the invention, the method further includes determining the mutation site in the genome of at least one hyper-invasive mutant microorganism to identify an invasive hil gene. When a transposon utilizing a constitutive or inducible promoter is used, the identification of such genes can be readily accomplished utilizing a labeled transposon as a probe to a genomic library of the mutant microorganism to localize the site of transposon insertion. Sequencing downstream from the promoter sequence in the transposon and identification of an open reading frame results in identification of at least a portion of a hil gene and the deduced amino acid sequence. However, since it is possible for the transposon to integrate into a site other than the beginning of a transcription unit of the hyper-invasive gene, sequencing of the mutant microorganism from the other end of the transposon or upstream from the identified insertion site in the parental microorganism can be performed to confirm the entire open reading frame of the hil gene.

If there is no known sequence correspondence or if further analysis is desired, the thus identified nucleic acid containing the open reading frame either with the transposon promoter, or in conjunction with a different promoter system, is cloned and thereafter used to transform a non-invasive microorganism such as a non-invasive E. coli. Those non-invasive microorganisms which acquire an invasive phenotype, e.g., based upon their invasiveness of cultured mammalian cells as described herein, contain the nucleic acid of a hil gene. Those which do not confer an invasive phenotype are presumed to encode a hil gene which is an activator of one or more invasive genes.

Activator hil genes are useful to attenuate the invasive capability in the same or different species of microorganism. For example, if coupled to a constitutive or inducible promoter other than that normally associated with the wild-type gene, such constructs can be used to transform other species of the same microorganism to restore invasive capability (if the microorganism lacks invasiveness or has substantially reduced invasive capability) or to increase the invasiveness of an otherwise invasive microorganism.

Regardless of whether the hil gene encodes a protein capable of imparting invasiveness or is an activator of invasiveness, various modifications can be made to the genomic sequence encoding such a hil gene to attenuate the invasiveness of the microorganism.

Microorganisms having attenuated invasiveness by mutation of one or more hil genes are particularly useful as vaccines, either to generate an immune response to the attenuated microorganism or to one or more proteins encoded by exogenous DNA contained within the organism. Such mutations include the substitution, insertion or deletion of one or more nucleotides of the hil gene, preferably within the protein encoding region, although modification within an expression regulation sequence of the selected gene is also contemplated. The techniques for such modifications are well known to those skilled in the art and involve routine manipulations once a gene is identified and selected for modification.

Examples of nucleotide substitution include modification of one or more codons to a premature translation termination signal, substitution of nucleotides within the ribosome binding site, the promoter sequences etc. Examples of nucleotide insertion include transposon insertion into the protein encoding region or regulatory regions required for transcription or translation. While the foregoing are capable of attenuating the invasiveness of a particular microorganism, they are not preferred when the mutated microoorganism is to be used as a vaccine. This is because of the relatively high potential for reversion to the wild-type phenotype. Accordingly, when used as a vaccine, the preferred modification of the invasive gene is deletion of nucleotides, preferably deletion of most, and most preferably all of the hil gene, including the protein encoding and expression regulation sequences.

For example, *Salmonella typhimurium* is an invasive microorganism which as described herein contains a hil locus in addition to the invasive inv locus. The invasive character of the wild-type microorganism often results in systemic infection including septicemia. As a consequence, this microorganism has not been widely used as a live vaccine. However, an attenuated *Salmonella typhimurium*, wherein a hil gene has been inactivated by mutation, such as by deletion of the gene as described in the Examples herein, has an attenuated invasive phenotype wherein the invasiveness of the microorganism is mediated primarily by the inv or other invasive gene rather than the hil gene. Since the hil gene is believed to be responsible for the hyper-invasiveness of the organism, hil mutants are expected to be far less invasive than the wild-type organism. Such mutant Salmonella therefore should exhibit sufficient invasiveness to bring about a localized low grade infection, e.g. localized to the Peyers patch, sufficient to cause an effective immune response to the mutant Salmonella, but insufficient invasiveness to cause systemic infection. Of course, other non-reverting mutations which attenuate survival in a mammalian host, as described above, can be combined with the hil mutation to further minimize the likelihood of deleterious infection.

In addition to the foregoing use as a live attenuated vaccine, such hil mutated Salmonella can also be used as a vaccine to confer protection against other pathogens. When so used, exogenous DNA encoding an immunogen such as one or more surface membrane proteins, capsid proteins or envelope proteins from a selected pathogen, e.g., virus, prokaryote or eukaryote, is incorporated into the mutant Salmonella in a DNA construct which facilitates expression of the encoding DNA. Such constructs optionally encode a form of the immunogen that contains a functional secretory signal, transmembrane region and anchor region such that the immunogen is presented on the surface of the mutant Salmonella to facilitate an immunogenic response.

Antigens of interest may come from a wide variety of sources, including bacteria, such as Bordatella, Salmonella, Neisseria, Pneumococcus, Shigellae, Yersinia, Cholera, Meningococcus, Listeria, Mycobacterium, etc.; viruses, such as HTLV-I, -II, and -III, FeLV, HSV-1 and -2, Adenovirus, Varicella, Vaccinia, Hepatitis, Influenza, Measles, Rubella, Smallpox, Typhoid, Yellow Fever, etc. fungi, such as Candida, Microsporum, Tricpohyton, Arthroderma, Cryptococcus, Blastomyces, Histoplasma, Coccidroides, Paracoccidroides, Aspergillus, Phycomycetes, Sporotorax, Epidermophyton, etc. other pathogenic microorganisms, such as Chlamydia, Giardia, etc.

The organisms may be administered in any convenient form as a vaccine. Normally, physiologically acceptable carriers will be employed, such as deionized water, phosphate buffered saline (PBS), aluminum hydroxide, sugar or the like. Usually, the dosage will be determined empirically; about $10^4$ to $10^{10}$ cells will be administered to a human host, with proportionate administration based on size to other mammalian hosts. Generally, there will be a first administration, followed by one or more administrations at two to six week intervals. The particular amount administered will depend upon a number of factors, such as the viability of the invasive microorganism in the host, the concentration of the antigen on the surface of the pathogen, the number of different antigens which are present, the level of immune response to the particular antigen(s), and the like. Administration may be orally, by injection, intravenously, intraarterially, subcutaneously, intraperitoneally, etc. The manner of administering live vaccines is well established and may be found in such texts as Basic and Clinical Immunology, eds. Stites, Stobo, Fudenberg and Wells. 4th ed. Lange Medical Publications, Los Altos, Calif., 1982.

The microorganisms having attenuated invasiveness may also be used to prepare antisera for passive immunization. Thus, γ-globulin could be prepared which has antibodies to a broad spectrum of pathogens and for strains of a particular pathogen. The γ-globulin may be isolated and purified from serum by ammonium sulfate precipitation and fractionation according to known techniques. Administration to a mammalian host will generally be in amounts of 50 to 500 mg/kg of host in any physiologically acceptable carrier. Administration will usually be by injection, e.g., intravenously. The attenuated microorganism may also be used in assays for detecting the presence of antibodies to the antigens foreign to the attenuated microorganism or the antigens themselves.

If desired, one or more invasive hil genes (i.e., those which are capable of conferring an invasive phenotype to an otherwise non-invasive microorganism) can be modified for introducing invasiveness to another microorganism. For example, the regulatory signals, particularly the transcription initiation signal, may be modified by the addition or substitution of the native transcriptional initiation region with a transcriptional region associated with a different gene. In this way, one can provide for low or high levels of constitutive or inducible expression of the nucleic acid encoding for hil invasive capability. Various transcriptional initiation regions or promoters are available, which are temperature sensitive, are inducible in the presence of various metabolites or nutrients, and the like. Therefore, a transcriptional initiation region may be employed which is regulated by the recipient microorganism host and the hil invasive capability may be activated or inactivated by physically or chemically changing the environment of the recipient host. Thus, nutrients and metabolites such as glucose, tryptophan, histidine, galactose, lactose, may be employed to induce or repress the expression of one or more invasive hil genes. The inducible transcriptional regulatory region may be selected in accordance with the mammalian host, depending upon whether the coinducer or corepressor is naturally found in the mammalian host or can be administered to the host.

A shuttle vector may be provided in the recipient microorganism host which has the capability for replication in a mammalian cell as well as the recipient microorganism, where the shuttle vector may exist as an episomal element or become integrated into the mammalian cell genome. In this manner, recipient hosts may be used directly for the transfer of exogenous DNA into a mammalian cell host with high efficiency. Thus, a wide variety of genetic capabilities can be introduced into mammalian hosts, for example, the expression of lymphokines, hormones, enzymes, surface membrane proteins, and the like, such as interferons, interleukins, growth factors, hydrolases, oxidoreductases, receptors, antibodies, histocompatibility antigens, etc.

The non-invasive host which is modified to become invasive may be prokaryotic or eukaryotic and will be selected depending upon its ultimate purpose. Where the organism is to be the vehicle for transfer of DNA into mammalian cells in culture, then any convenient organism may be employed, particularly one which may be used for cloning of the DNA to be transferred. Therefore, many of the strains of *E. coli*, e.g., K12, may be employed as the recipient microorganism which is modified to become invasive. Where the modified microorganism host is to be employed as a vaccine, the host will normally be selected so as to be innocuous (non-pathogenic), to be capable of being viable extracellularly for an extended period of time, preferably at least about 3 days in the vaccinated host, and to be subject to ready clearance in the vaccinated host. Desirably, the modified recipient microorganism will be free of pyrogens, toxins, or other disease symptom causing factors. By innocuous is intended that regardless of the dose or route, no disease will be observed with an immunocompetent host. While pathogenic microorganisms may be employed, particularly attenuated pathogenic microorganisms, these are not preferred, since there is a possibility of reversion to pathogenicity. Microorganism hosts which may be used for modification to invasive capability include besides *E. coli*, members of the genus Staphylococci, Pneumococci, Streptococci, e.g., mutants, Neisseria, e.g., catarrhalis, Veillonella, Lactobacilli, Corynebacteria, Clostridia, Hemophilic bacilli, Bacteroides, Actinomycetes, Spirochetes, Mycoplasma, etc.

The manner in which the genetic capability for invasiveness is introduced into the recipient microorganism may be any of the convenient techniques including transformation, e.g., calcium precipitated DNA, transfection, transduction, conjugation, fusion, etc. Applicable techniques may be found in Maniatis et al., A Laboratory Manual, Cold Spring Harbor Laboratory, Cold Spring Harbor, N.Y., 1982. As already indicated, a marker will normally be present which allows for selection of those microorganisms which have received the invasive genetic capability. The organisms may then be grown in an appropriate nutrient medium and used as appropriate.

Sequences encoding all or a portion of a hil gene may be used for diagnosing pathogenicity or virulence. Such fragments are preferably of at least about 50 bp, preferably at least about 100 bp or extensions thereof including the entire hil gene coding region or locus.

The following examples are offered by way of illustration and not by way of limitation.

EXAMPLE 1

The following describes the identification of the hil gene in *Salmonella typhimurium* utilizing a novel approach based on the finding that Salmonella invasiveness is regulated by oxygen.

Bacteria grown aerobically are less invasive than bacteria grown under oxygen-limiting conditions (Lee, C. A. and Falkow, S. (1990) *Proc. Natl. Acad. Sci. USA* 87:4304–4308; Ernest, R. K., Dombroski, D. M. and Merrick, J. M. (1990) *Infect. Immun.* 58:2014–2016, and Schiemann, D. A. and Shope, S. R. (1991) *Infect. Immun.* 59:437–440). It was reasoned that mutants which constitutively express Salmonella invasion factors might enter epithelial cells even when grown aerobically. The following describes the identification and characterization of such hyper-invasive *S. typhimurium* mutants.

In order to identify *S. typhimurium* genes involved in epithelial cell entry, mutants were selected that entered Hep-2 cells when grown under repressing, aerobic culture conditions. Two types of transposons were used to generate bacterial mutations, transposons that disrupt genes (Tn10 and Tn5) and one transposon (Tn5B50) that, in addition to disrupting genes, can cause constitutive expression of genes from the neo promoter at one end of the transposon. Three classes of mutations were found which increased the ability of aerobically grown *S. typhimurium* to enter Hep-2 cells. One class of mutations disrupt the che operons and result in a non-chemotactic phenotype. The second class of mutations revealed that defects in rho, which encodes an essential transcription termination factor, result in hyper-invasiveness. The third class of mutations was obtained from mutagenesis with Tn5B50, suggesting that their increased invasiveness is due to constitutive expression of a gene(s) from the exogenous neo promoter. Analysis of this third class of mutations identified a *S. typhimurium* locus hil (hyper-invasion locus) which is essential for bacterial entry into epithelial cells. The results suggest that hil encodes an invasion factor or an activator of invasion factor expression. hil maps between srl and mutS near minute 59.5 of the *S. typhimurium* chromosome, a region adjacent to other loci that have been identified as required for *S. typhimurium* invasiveness and virulence.

Genetic and Molecular Biological Techniques

P22-mediated transduction was conducted as previously described (Davis, R. W., Botstein, D. and Roth, J. R. (1980) in Advanced Bacterial Genetics: A manual for genetic engineering (Cold Spring Harbor Laboratory, Cold Spring Harbor, N.Y.)). Isogenic rho$^{ts}$-111 and rho$^+$ strains were constructed by transduction of ilv::Tn10 from AA965 (Housley, P. R., Leavitt, A. D. and Whitfield, H. J. (1981) *J. Bacteriol.* 147:13–24) to SL1344 (Hoiseth, S. K. and Stocker, B. A. (1981) *Nature* 291:238–239) and screening for acquisition of temperature-sensitivity (rho$^{ts}$-111) or maintenance of temperature-resistance (rho$^+$). Tn5 insertions linked to Tn5B50-380 were isolated by P22-mediated transduction of Tn5 from pools of random EE251::Tn5 strains (see below) to SL1344::Tn5B50-380. Kanamycin-resistant transductants were replica-plated onto media containing kanamycin and tetracycline to identify those desired transductants that had consequently lost the Tn5B50 mutation.

DNA from P22 phage particles was isolated from mitomycin C-induced phage lysates of 70 Mud-P22 strains (N. Benson and B. Goldman, unpublished results; Gillen, K. L. and Hughes, K. T. (1991) *J. Bacteriol.* 173:2301–2310) by precipitation of phage with 3% polyethylene glycol (MW—8000) and 0.375M sodium chloride. Phage were resuspended in dilution buffer (Davis, R. W., Botstein, D. and Roth, J. R. (1980) in Advanced Bacterial Genetics: A manual for genetic engineering (Cold Spring Harbor Laboratory, Cold Spring Harbor, N.Y.)) before serial extraction with chloroform and phenol. Phage particle DNA was recovered by precipitation from the aqueous phase with ethanol in the presence of 0.3M sodium acetate.

*S. typhimurium* DNA flanking Tn5 or Tn5B50 mutations was cloned by selection of chromosomal DNA fragments containing the antibiotic-resistance gene of the transposon. The restriction pattern of the genetic locus associated with hyper-invasion was deduced by restriction analysis of these DNA fragments as well as their use in Southern analysis of *S. typhimurium* chromosomal DNA. Collectively, four DNA fragments contain the 20 kb of *S. typhimurium* chromosomal DNA depicted in FIG. 1, except for 2.6 kb at the extreme left end and 2 kb downstream of the third BamHI site. DNA probes were labelled with $^{32}$P-dCTP by nick-translation and DNA-DNA hybridization was conducted on nitrocellulose filters as previously described (Maniatis, T., Fritsch, E. F. and Sambrook, J. (1982) in Molecular Cloning: A laboratory manual (Cold Spring Harbor Laboratory, Cold Spring Harbor, N.Y.)).

DNA flanking Tn5-317 was cloned by selection for a BamHI chromosomal DNA fragment from EE251::Tn5-317 containing the kanamycin-resistance gene of Tn5. The sequence of *S. typhimurium* DNA flanking the Tn5 was determined by a chain-termination sequencing method (U.S. Biochemical, Sequenase 2.0, Cleveland, Ohio) using a partner complementary to the end of 1S50.

Bacterial and Tissue Culture Growth Conditions

Bacterial strains were grown in LB broth (Luria-Bertani; 1% Bacto-tryptone (Difco), 0.5% Bacto-yeast extract (Difco), 0.8% sodium chloride) or on LB agar (GIBCO). Media were supplemented with antibiotics when necessary; 100 µg/ml ampicillin, 25 µg/ml kanamycin, 100 µ/ml streptomycin and/or 10 µ/ml tetracycline. Strains were grown at 37° C., except that those used to examine the effect of rho$^{ts}$-111 were grown at 30° C. Two different growth conditions were used to assess the effect of oxygen limitation on *S. typhimurium* invasiveness. Aerobic cultures were prepared by first growing bacteria to stationary phase. Stationary phase cultures were prepared by inoculating 2 ml of LB broth in 16×150 mm borosilicate tubes with bacteria from a colony. After rolling the tubes on a rotator drum for approximately 20 hours, the bacteria were in stationary phase for at least 12 hours. Approximately $10^6$ colony forming units (cfu) from such stationary phase cultures were then inoculated into 1 ml of LB broth in tubes. Aerobic cultures with a final density of ~$10^8$ cfu/ml were obtained after placing the tubes on a rolling rotator drum for 2 to 3 hours. Oxygen-limited cultures were prepared by inoculation of 5 ml of LB broth in 16×150 mm tubes with ~$10^4$ cfu/ml. The tubes were incubated without agitation overnight until the cultures reached a density of $5\times10^8$ to $10^9$ cfu/ml.

HEp-2 cells (ATCC CCL23), a line established from a human epidermoid carcinoma, were grown without antibiotics in RPMI 1640 medium (Whittaker, Walkerville, Md.) supplemented with 5% fetal bovine serum (GIBCO). Monolayers for bacterial invasion were prepared by seeding ~$10^5$ cells into each well of a 24-multiwell tissue culture plate and incubating overnight at 37° C. in 5% $CO_2$.

Transposon Mutagenesis of *Salmonella typhimurium*

*S. typhimurium* strain SL1344 was mutagenized with Tn10 using a phage lysate from DB5204 (Davis, R. W., Botstein, D. and Roth, J. R. (1980) in Advanced Bacterial Genetics: A manual for genetic engineering (Cold Spring Harbor Laboratory, Cold Spring Harbor, N.Y.)). Tails were added to the defective P22 phage particles by incubation with extracts from *E. coli* 294/pPB13 (Sauer, R. T., Krovatin, W., Poteete, A. R. and Berget, P. B. (1982) *Biochemistry* 21:5811–5815). Two SL1344::Tn10 pools were generated, each containing 1,000 to 5,000 independent transposon mutants.

*S. typhimurium* strain EE251, a spontaneous streptomycin resistant derivative of SL4012 (Collins, A. L. and Stocker, B. A. (1976) *J. Bacteriol.* 128:754–765) was mutagenized with Tn5 or with Tn5B50 using a delivery system based on plasmid pRTP1 (Stibitz, S., Black, W. and Falkow, S. (1986) *Gene* 50:133–140). Initially, each transposon was moved by transposition from lambda derivatives (Simon, R., Quandt, J. and Klipp, W. (1989) *Gene* 80:161–169) to pRTP1 in the non-suppressing *E. coli* host strain MC4100. pRTP1::Tn5 and pRTP1::Tn5B50 were selected such that the transposon insertion did not disrupt the bla or rpsL genes on the plasmid. The mutagenesis system is based on the fact that strain EE251 contains a streptomycin-resistant allele of rpsL which is phenotypically recessive to the streptomycin-sensitive rpsL allele on the pRTP1 derivatives. In this way, transposition of Tn5 or Tn5B50 onto the genome of strain EE251 and subsequent loss of the plasmid can be selected for by growth of such EE251::Tn mutants in the presence of streptomycin and kanamycin (for Tn5; or tetracycline for Tn5B50).

For example, to generate one pool of EE251::Tn5 mutants, an exponentially growing culture, derived from a single colony of EE251/pRTP1::Tn5, was diluted and 5,000 to 10,000 cfu were plated onto L agar containing kanamycin. The plate was incubated overnight at 30° C. to allow growth of the colonies. In order to select for the EE251::Tn5 mutants within each colony, the colonies were replica plated onto L agar containing streptomycin and kanamycin. The replica plate was incubated overnight at 37° C. and the streptomycin resistant, kanamycin-resistant colonies were scraped from the agar and pooled. The replica plating procedure also serves to reduce the effect of unequal representation of transposon mutations that occurred at different times during growth at 30° C. since each independent mutant can only grow to the size of a colony on the selection medium. Using this procedure, almost every original kanamycin-resistant colony gave rise to an independent streptomycin-resistant, kanamycin-resistant colony on the replica plate. The surprisingly efficient selection of these transposon mutants that have lost the dominant streptomycin-sensitive pRTP1 derivative is likely due to the random segregation properties of the colE1 plasmid (Ayala, S. J. and Gomez, E. M. (1989) *Mol. Microbiol.* 3:1745–1752). Approximately 0.2% of the cfu in each pool remained ampicillin-resistant and likely were streptomycin-resistant due to mutation of the rpsL gene on the pRTP1 derivative. Ten to 12 independent pools of EE251::Tn5 and EE251::Tn5B50 mutants were generated by this procedure.

Selection for Hyper-invasive *S. typhimurium* Mutants

The selection procedure is based on the fact that extracellular bacteria are killed by gentamicin whereas intracellular bacteria are protected from exposure to the antibiotic (Vaudaux, P. and Waldvogel, F. A. (1979) *Antimicrob. Agents Chemother.* 16:743–749). To enrich for mutants that can enter Hep-2 cells even when grown aerobically, two different aerobic cultures were grown from each independent pool of *S. typhimurium* transposon mutants. One-tenth of a ml of each culture was then inoculated into the medium overlying Hep-2 monolayers. Bacteria were allowed to enter the HEp-2 cells during a one hour incubation at 37° C. in 5% $CO_2$. The medium was then changed to RPMI 1640 containing 5% fetal bovine serum and 100 µ/ml gentamicin, so that the extracellular bacteria were preferentially killed during an additional two hour incubation. To release any intracellular bacteria, the monolayers were rinsed twice with phosphate-buffered saline (PBS) and incubated with 50 µl 1% Triton X-100 for 10 minutes at room temperature. The viable bacteria were recovered as a saturated bacterial culture by adding 1 ml of LB broth to each well and agitating the entire dish overnight. The next day, the saturated culture was used to prepare an aerobic culture and the enrichment procedure was repeated. After four sequential enrichment cycles, intracellular bacteria were released from the HEp-2 cells and directly plated onto LB agar. Enumeration of the cfu released from each monolayer indicated which wells contained mutant strains that were more invasive than the wild-type *S. typhimurium*. Single colonies from such wells were purified and analyzed.

Mutant Analysis

*S. typhimurium* transposon mutants obtained from the selection procedure were (1) assayed for their ability to enter HEp-2 cells (see below), (2) reconstructed into both SL1344 and EE251 strain backgrounds, crossing out the transposon mutation by P22-mediated transduction and (3) re-tested after reconstruction for invasiveness. From this analysis, independent transposon mutations which were found to result in at least a 10-fold increase in aerobic invasiveness were saved and analyzed further.

Bacterial invasiveness was assayed by inoculating ~$10^7$ cfu into the medium overlying a HEp-2 monolayer. Bacteria were allowed to enter the HEp-2 cells during a one hour incubation. After a two hour treatment with gentamicin, the cell monolayer was rinsed with PBS and disrupted by incubation with 0.2 ml 1% Triton X-100. Each sample was vigorously mixed with 0.8 ml LB broth using a pasteur pipet and the viable bacteria were quantitated by plating for cfu on LB agar. Differences in bacterial invasiveness were verified by Giemsa staining of infected monolayers and direct microscopic observation of bacterial association with cells.

Identification and Characterization of Hyper-Invasive *S. typhimurium* Mutants Tn10, Tn5 and Tn5B50 mutants of *S. typhimurium* were selected by their ability to enter epithelial cells after aerobic growth. Positive selection of such mutants by their ability to resist killing by gentamicin in infected HEp-2 cells allowed their identification from large pools of random mutants. Sixteen independent transposon mutations, three Tn/10, five Tn5 and eight Tn5B50 insertions, were found to increase the ability of aerobically grown *S. typhimurium* to enter HEp-2 cells by 13- to 74-fold (Table I).

TABLE I

Effect of representative transposon mutations on S. typhimurium SL1344 invasiveness

| SL1344 derivative | Relative Invasoveness* | |
|---|---|---|
| | aerobic growth condition | low oxygen growth condition |
| wild-type | 1 ± 0.2 | 43 ± 2 |
| ::Tn10-181 | 13 ± 4 | 54 ± 10 |
| ::Tn10-177 | 16 ± 5 | 62 ± 8 |
| ::Tn5B50-378 | 74 ± 7 | 373 ± 60 |
| ::Tn5B50-380 | 18 ± 8 | 96 ± 9 |

*Values represent the mean and standard error of multiple assays and were normalized such that the invasiveness of aerobically grown SL1344 equals one. The actual percentage of the aerobic SL1344 inoculum that entered HEp-2 cells in one hour was 0.11 0.018%.

In order to determine whether the insertions affect the same or different genes, the mutations were mapped relative to one another by transduction. This was possible since Tn5 encodes kanamycin-resistance whereas Tn/10 and Tn5B50 encode tetracycline resistance. For example, Tn10-181 was found to be >95% linked to Tn5-300 since transduction of Tn/10-181 into a strain carrying Tn5-300 resulted in frequent loss of kanamycin-resistance. In this way, the sixteen mutations were found to define three linkage groups; eleven were in group A, three were in group B and two were in group C.

Groups A and B each contained Tn10, Tn5 and Tn5B50 mutations. In contrast, group C contained only Tn5B50 mutations, specifically, Tn5B50-378 and Tn5B50-380.

The transposons Tn10 and Tn5 insert into genes and disrupt their function. However, Tn5B50, which contains the constitutive neo promoter at one end, cannot only cause genetic disruption but can also result in constitutive expression of an intact gene(s) from the neo promoter. The isolation of both Tn10 and Tn5 mutations in groups A and B indicate that disruption of genes increase the ability of these mutants to enter HEp-2 cells. In contrast, the identification of the C mutants solely from Tn5 B50 mutagenesis indicates that these mutants are better able to enter HEp-2 cells due to the expression of a gene(s) from the neo promoter at the end of the transposon.

Identification of che Mutants

In order to identify the genetic lesion in group A mutants, *S. typhimurium* DNA flanking the Tn10-181 group A insertion was cloned, sequenced and examined for homology to previously identified genes. Tn10-181 was found to be inserted in one of the chemotaxis (che) operons and results in a non-chemotactic phenotype. The che genes allow Salmonella to bias their movement toward attractants or away from repellents by modulating the frequency of smooth swimming versus tumbling behavior (Neidhardt, F. C., Ingraham, J. L., Low, K. B., Magasanik, B., Schaechter, M. and Umbarger, H. E. (1987) in *Escherichia coli* and *Salmonella typhimurium:* cellular and molecular biology (American Society for Microbiology, Washington, D.C.)). Microscopic and swarm plate analysis of the eleven group A mutants confirmed that all are non-chemotactic, specifically due to their inability to tumble (results not shown).

Identification of rho Mutants

In order to identify what genetic sequence was disrupted in the group B mutants, *S. typhimurium* DNA flanking the Tn5-317 group B insertion was cloned, sequenced and examined for homology to previously identified genes. By inference from what is known in *E. coli*, Tn5-317 was found to be inserted between the -10 and -35 regions of the promoter for the *S. typhimurium* rho gene. While the Tn5-317 insertion may affect the end of the trx transcript which, in *E. coli*, terminates in the same region, the position of the insertion more likely affects the expression of rho (Matsumoto, Y., Shigesada, K., Hirano, M. and Imai, M. (1986) *J. Bacteriol.* 166:945–958). In order to examine whether defects in rho expression result in hyper-invasiveness, isogenic $rho^{ts}$-111 and $rho^+$ derivatives of SL1344 were constructed and tested for invasiveness. The $rho^{ts}$-111 mutation was found to increase bacterial invasion to an even greater extent than the group B transposon mutations (data not shown).

Characterization of the Third Hyper-Invasive Locus (hil)

Tn5B50-378 and Tn5B50-380 were found to define the C linkage group of hyper-invasive mutations. Initially, two independent Tn5 insertions, Tn5-428 and Tn5-429, were isolated by virtue of their linkage to Tn5B50-380. Transduction of the Tn5 mutations into strains containing the Tn5B50 mutations demonstrated that the hyper-invasive mutations were linked since, the two Tn5 mutations were found to be closely linked to both Tn5B50 mutations.

Defined Mud-P22 strains were utilized to determine where the Tn5B50 mutations lay in the *S. typhimurium* genome. Fragments of *S. typhimurium* DNA flanking the Tn5-428 and the Tn5B50-380 mutations were used as probes to test for hybridization with phage particle DNA from 70 Mud-P22 strains. The results showed that Tn5-428 and Tn5B50-380 lie between proU at minute 57.5 and cysHIJ at minute 60 on the *S. typhimurium* chromosome, since in each case, the flanking DNA hybridized to phage particle DNA from the proU1884::Mud-P, cysH1J1574::MudP and purG2149::MudP strains. Subsequent P22-mediated transductional analysis revealed that Tn5-429 is weakly linked (<0.2%) to both srl and mutS. Only 3 of 3569 and 3 of 1833 transductants lost Tn10 mutations in srl and mutS, respectively, as a result of transduction with Tn5-429. Presumably, the gene order is srl -Tn5 - mutS - cys.

The relative positions and orientations of the Tn5B50 mutations in the chromosome were deduced by restriction analysis of chromosomal and cloned DNA from SL1344 and the transposon mutants (FIG. 1A). The results show that the neo promoters of both Tn5B50 mutations are oriented in the same direction and that Tn5B50-378, the strongest hyper-invasive mutation, lies 6.4 kb downstream of Tn5B50-380. In addition, the site of Tn5-429 insertion was found to lie 2 kb upstream of that of Tn5B50-380 (not shown). We have named this locus hil for hyper-invasion locus.

Characterization of a hil Deletion Mutant

The phenotypic and molecular analysis of the group C hyper-invasive mutations suggests that there is a gene(s) downstream of Tn5B50-378 that acts positively on expression of *S. typhimurium* invasiveness. If this is the case, deletion or disruption of the hil locus might result in loss of invasiveness. Fortuitously, 10 kb of chromosomal DNA downstream of the Tn5B 50-380 mutation was found to be deleted in the Tn5-428 mutant strain (FIG. 1A). Tn5-428 was identified as promoting loss of the tetracycline-resistance phenotype of the Tn5B 50 - 380 mutation by transduction. However, analysis of chromosomal and cloned DNA from the Tn5-428 mutant suggests that the initial recombination of Tn5-428 into the chromosome did not remove the Tn5B50 mutation, instead, tetracycline-resistance apparently was lost by subsequent homologous recombination and deletion between 1550 elements of Tn5B 50 and Tn5.

Analysis of the effect of the hil deletion mutation on bacterial entry into HEp-2 cells showed that this region is essential for expression of *S. typhimurium* invasiveness. Even when grown under low oxygen conditions, the hil deletion mutant was 1000-fold less able to enter HEp-2 cells than the comparably grown parental strain (results not shown).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid comprising the hyper-invasive locus of *Salmonella typhimurium* located on the 20 kb fragment shown in FIG. 1A.

2. A nucleic acid comprising transcriptional and translational initiation and termination regulatory regions functional in a microorganism host and the hyper-invasive locus of *Salmonella typhimurium* located on the 20 kb fragment shown in FIG. 1A wherein said initiation region is other than a wild-type initiation region of the hil locus, and wherein said regulatory regions are capable of causing expression of all or part of said locus.

3. An isolated nucleic acid which comprises a mutated *Salmonella typhimurium* nucleic acid which confers a hyper-invasive phenotype in *Salmonella typhimurium*, wherein the mutation is in the hyperinvasive locus located on the 20 kb fragment shown in FIG. 1A.

4. An isolated nucleic acid according to claim 3 further comprising transcriptional and translational initiation and termination regulatory regions.

* * * * *